United States Patent
Rigby

(10) Patent No.: US 9,027,390 B1
(45) Date of Patent: May 12, 2015

(54) SYSTEM AND METHOD OF DETERMINING SOURCES OF WATER INFILTRATION/INFLOW INTO A SEWER SYSTEM

(71) Applicant: Gene Rigby, Marion, OH (US)

(72) Inventor: Gene Rigby, Marion, OH (US)

(*) Notice: Subject to any disclaimer, the term of this patent is extended or adjusted under 35 U.S.C. 154(b) by 0 days.

(21) Appl. No.: 13/836,205

(22) Filed: Mar. 15, 2013

Related U.S. Application Data

(63) Continuation-in-part of application No. 12/859,696, filed on Aug. 19, 2010, now abandoned.

(60) Provisional application No. 61/235,206, filed on Aug. 19, 2009.

(51) Int. Cl.
*B05D 5/00* (2006.01)
*G01N 21/88* (2006.01)
*G01N 33/32* (2006.01)

(52) U.S. Cl.
CPC ... *B05D 5/00* (2013.01); *G01N 33/32* (2013.01); *G01N 21/88* (2013.01)

(58) Field of Classification Search
CPC ......... G01N 33/32; G01N 21/88; B05D 5/00; B05D 1/02; B05D 3/007; B05D 1/26; B05D 2451/00; B05D 3/0486; Y10S 252/964; Y10S 252/96; Y10S 252/963; Y10S 428/913; Y10S 524/903; G01M 3/12
USPC ......... 73/150 R, 150 A, 40.7, 40, 104; 427/8, 427/10, 9; 118/712; 106/31.6; 156/64; 252/964
See application file for complete search history.

(56) References Cited

U.S. PATENT DOCUMENTS

| | | | |
|---|---|---|---|
| 3,597,263 A * | 8/1971 | Bancroft | 422/429 |
| 3,739,089 A * | 6/1973 | Latall | 348/84 |
| 4,373,381 A | 2/1983 | Kulp et al. | |
| 5,058,805 A * | 10/1991 | Anderson et al. | 239/3 |
| 5,152,904 A * | 10/1992 | Kedem et al. | 210/711 |
| 5,467,640 A | 11/1995 | Salinas | |
| 6,621,516 B1 * | 9/2003 | Wasson et al. | 348/84 |
| 7,164,476 B2 | 1/2007 | Shima et al. | |
| 2005/0005716 A1 * | 1/2005 | Harris | 73/865.8 |
| 2005/0236042 A1 * | 10/2005 | Hansen et al. | 137/236.1 |
| 2009/0120215 A1 * | 5/2009 | Jacobson et al. | 73/865.8 |

FOREIGN PATENT DOCUMENTS

WO   WO 2009058891 A2 *   5/2009   ............. G01M 3/20

OTHER PUBLICATIONS

"American Gas & Oil Co. Hydrostatic Testing." American Gas & Chemical Co. Hydrostatic Testing, N.p., Dec. 16, 2000. Web. Oct. 1, 2012. <http://www.amgas.com/hydro1.htm>.

* cited by examiner

*Primary Examiner* — Hezron E Williams
*Assistant Examiner* — Marrit Eyassu
(74) *Attorney, Agent, or Firm* — James R. Eley; Eley Law Firm Co., LPA

(57) ABSTRACT

A system for identifying sources of external fluid infiltrating or leaking into a sanitary sewer system. An apparatus applies a substantially uniform coating to the surface of inner walls of a portion of the sewer system. The system also includes means for observing and recording the initial condition of the coated surface, means for observing and recording subsequent conditions of the coated surface, and means for comparing the initial condition of the coated surface with subsequent conditions to detect a predetermined change in the condition of the coated surface. The change in the condition of the coated surface indicates the source of the infiltration of water into the sewer system.

21 Claims, 3 Drawing Sheets

SYSTEM AND METHOD OF DETERMINING SOURCES OF WATER INFILTRATION/INFLOW INTO A SEWER SYSTEM

This application is a continuation-in-part of U.S. utility patent application Ser. No. 12/859,696, filed Aug. 19, 2010, which claims priority to U.S. provisional application 61/235,206, filed Aug. 19, 2009, the entire contents of each being hereby incorporated by reference thereto.

FIELD

The present invention relates generally to a system and method for determining water leakage, in particular to a system and method for determining water leakage into buried pipe and underground manholes.

BACKGROUND

External sources of water entering a sanitary sewer system is problematic worldwide. For example, when groundwater infiltrates the sanitary sewer system an associated water treatment system may become overtaxed, since it must handle the added water. Since groundwater does not generally need to be treated, this often leads to wasteful increases in processing costs and equipment costs.

In addition, when the demand placed upon the sanitary sewer collection system exceeds its capacity sewage at the treatment facility may prematurely overflow into the environment prior to being fully treated. Likewise, overtaxed sewer systems may hydraulically back up into customers' residences and businesses, often causing overflow of untreated sewage directly into waterways. This is due to the treatment system being forced to convey and treat more water than its intended design capacity. This is a growing problem, particularly as infrastructures age and sewer systems become more porous to the environment.

Groundwater or rainwater entering the sanitary sewer system, commonly referred to as infiltration/inflow ("I/I"), may result from a number of events, such as heavy rains, either locally or remotely (i.e., upstream), flooding, melting snow/ice, and water line breaks, hereinafter referred to as "I/I events." In this context, groundwater is not necessarily emanating from the ground; rather, it is filtering through the ground and into the sewer system. This water is drawn by gravity to its lowest point, through one or more leaks within the sanitary sewer system, if available. The source of I/I into the sanitary sewer system may include defects in one or more of main lines, lateral lines and manholes. In particular, some of the sources of I/I in a sanitary sewer system include, but are not limited to, pipe cracks, poor pipe joints, poor lateral or manhole pipe connections, and defects in manholes walls, joints, castings, and lids.

There are a multitude of sources of I/I into a sanitary sewer system that ultimately flow to an associated wastewater treatment plant, causing treatment plant capacity problems. Generally, the intensity and duration of rainfall, along with existing groundwater conditions, dictate the amount and intensity of I/I. Typically, the gravity main line sewer, lateral sewers and manholes are all installed on a gravel foundation and are buried within gravel. A consequence of this arrangement is that the gravel provides a pathway for the water to flow by gravity, following the path of least resistance, to the various leakage defects within the sanitary sewer system that act as sources for I/I.

Currently, locating these costly leaks relies much on happenstance, such as someone being in the right place and at the right time to observe a leak during an active I/I event. However, humanly-observed I/I occurrences in real-time are relatively rare; accordingly, many leaks may continue unabated for years before they are detected, if ever.

If an I/I leak is detected it may be readily repaired using any number of suitable remedial measures, such as grouting, surface coatings, lining sewer pipes, replacing faulty pipes, and so on. The challenge facing sewer maintenance personnel is detecting and locating the leaks, which usually occurs only during an I/I event. Adding to the detection problem is a timing element, as some leaks may not occur until days following the rain event because of the distance of the defect from the I/I event, among other factors.

Previous methods for detecting and isolating points of I/I into a sanitary sewer system typically rely solely on visual identification. Consequently, such methods are difficult to perform, are time-consuming, and are expensive. One example of a current process for finding defects in sewer pipe is disclosed in U.S. Pat. No. 4,373,381 to Kulp et al. The process taught by Kulp requires sealing off the incoming pipes and performing a vacuum test on the manhole, which can be both complex and time-consuming. Another relatively complex and time-consuming process for locating defects in pipes involves installing a plug between two sections of pipe to form a seal. A section of the pipe is then pressure tested, as disclosed in U.S. Pat. No. 5,467,640 to Salinas.

Yet another process for finding I/I defects in pipes is disclosed in U.S. Pat. No. 6,621,516 to Wasson et al., which requires flooding the ground surrounding the pipe with phosphorescent dye and detecting the dye as it leaks into the pipe. This process requires substantial amount of time and is not necessarily indicative of the real-world characteristics of what occurs in a sewer system during a rain or I/I event. Wasson, et al., also disclose coating the inside of the pipe with a lacquer coating that is laced with ferromagnetic phosphorescent particles to indicate small cracks or other defects in a pipe when viewed under a black light illuminator. However, the existence of such defects does not necessarily mean that the defects are a source where actual I/I enters the pipe or manhole. Consequently, this can lead to costly and unnecessary repairs.

What is needed is a relatively simple system and method for indicating sources of I/I into a sanitary sewer system that will continue to indicate for some time after the event whether the I/I entered the sewer system at these various defects, to eliminate the need to be physically present and visually observe the I/I occurring.

SUMMARY

The system and method described herein provides a way to determine if buried sewer pipe or structure (e.g., a manhole) in a sanitary sewer system suffers from I/I without requiring the physical presence of maintenance personnel to observe the I/I event in real-time.

In one embodiment this is accomplished by preparing an inner surface of pipe or structure by cleaning it and then coating select portions of the inner surface with an environmentally safe indicia material that is compatible with the surface area to be coated, and that provides either a lasting or temporal indication as to whether it has been impacted by a subsequent I/I event. The indicia consists of a flowable coating material which exhibits physically observable characteristics that may include staining/discoloration of the impacted area or a washing away of all or a portion of the coating that has been impinged upon. If the I/I enters through a defect in the pipe or structural wall the I/I will leave the coated surface stained or discolored, or the I/I may wash away at least a portion of the coated surface.

The process includes preparing the surface to be coated by removing environment elements such as dirt, scum, sediment and the like to produce an adherable surface. Next, a suitable coating is applied to the inner surface of the pipe/structure and is permitted to dry. Following application of the coating to the desired portions of the inner surface of the sanitary sewer system a baseline record may be made either by physical visual examination, or photographic or video recording means to produce a "before" condition. I/I events that follow then cause the coated area previously monitored and recorded to be discolored, stained or displaced/removed due to the various defects in the sanitary sewer system, the "after" condition. The observation of the coated area may be repeated more than once, depending upon the magnitude of the I/I event (e.g., rainfall intensity/duration and groundwater conditions) and the results of each observation may be recorded in order to determine the source and, potentially the magnitude, of the I/I. Recordation may comprise visual inspection and written reporting of the coated surfaces, photographing and time stamping the visual inspections, videotaping and time logging the inspections, or any combination thereof.

Utilizing the disclosed system and/or methodology enables maintenance personnel to determine the point of the I/I, and also to estimate the volume or otherwise quantify the severity of the leak by the amount of impact on the indicating coating. This enables maintenance personnel to selectively and efficiently effect repairs to only those structures in need, rather than sealing or replacing an entire length pipe or structure, thus providing for faster repairs and a significant savings of resources while greatly contributing to maintaining the integrity and efficiency of the sewage treatment system as a whole.

BRIEF DESCRIPTION OF THE DRAWINGS

Further features of the inventive embodiments will become apparent to those skilled in the art to which the embodiments relate from reading the specification and claims with reference to the accompanying drawings, in which:

DETAILED DESCRIPTION

Figure 1:
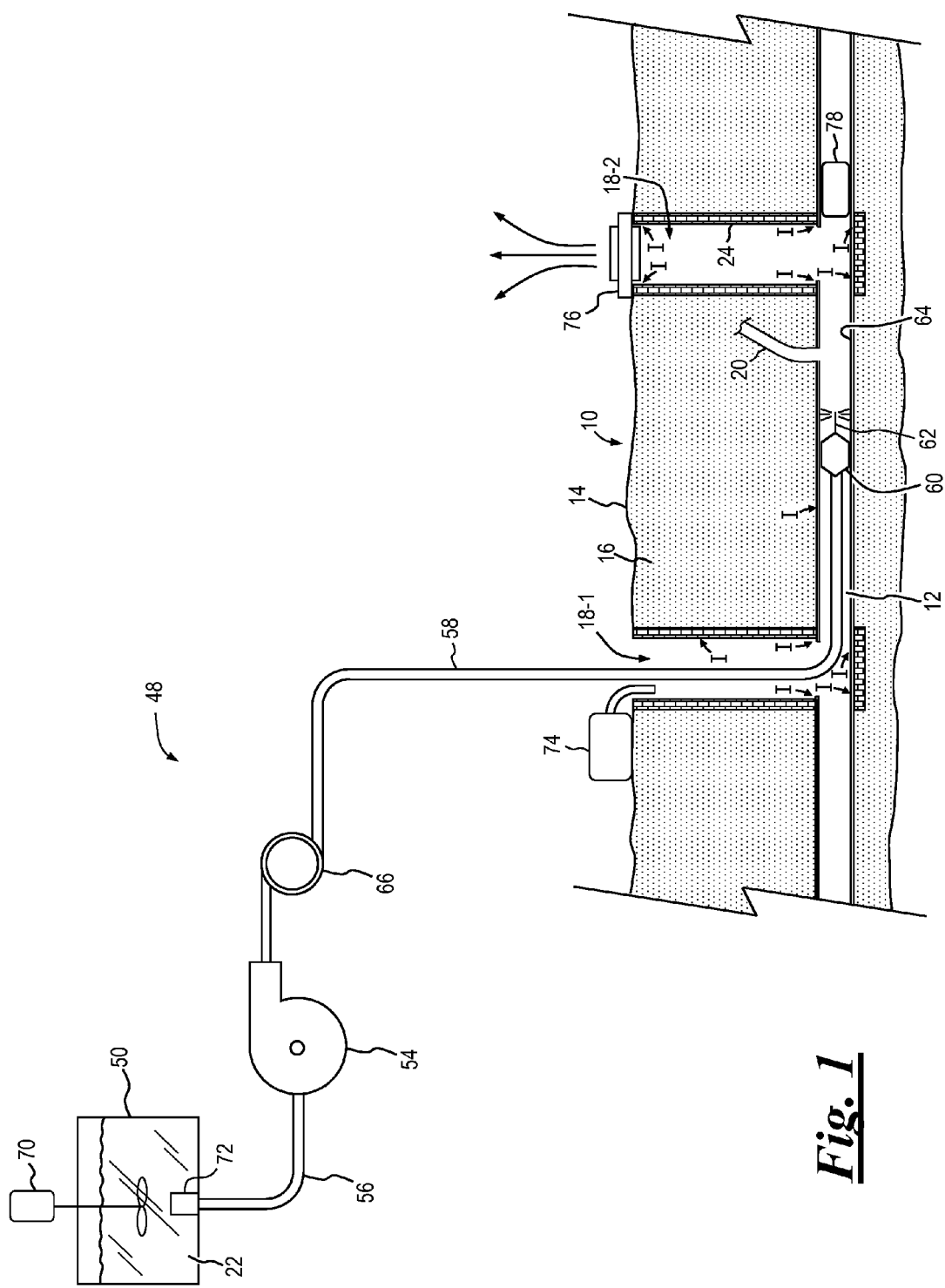
FIG. 1 is a schematic view of an aspect of the present disclosure depicting the general arrangement of a sanitary sewer system and the application of an indicia coating to the inner surface of a sewer pipe.

In the discussion that follows, like reference numerals are used to refer to like elements and structures in the various figures.

Referring to FIG. 1, a schematic diagram of a portion of a fluid-carrying structure, in particular a sanitary sewer system 10, is shown. Sewer system 10 includes one or more gravity sewer main lines 12 generally buried beneath a surface 14 of the ground 16. One or more junction points or maintenance access points, commonly referred to as "manholes" 18, extend between the surface 14 of the ground 16 and main line 12. In FIG. 1 a first manhole 18-1 and a second manhole 18-2 are shown, though sewer system 10 may have a greater or lesser number of manholes. Sewer system 10 may further include one or more gravity lateral sewer lines 20 that are connected to and in communication with main line 12. Lateral sewer lines 20 are individual lines that typically service a single facility or structure.

It should be noted that sewer system 10 typically further includes pump stations and force main lines (not shown). However, defects in force main lines are typically an exfiltration problem rather than an infiltration problem and thus are not discussed further here.

The majority of sewer system 10, including gravity flow sewer main lines 12, manholes 18, and gravity flow sewer lateral sewer lines 20 are substantially buried beneath the surface 14 of the ground 16 and are susceptible to receiving undesirable external fluids such as groundwater, i.e., "infiltration." Infiltration generally includes a leak (or leaks) in a sewer system that occurs at a relatively low rate for a relatively long period of time. Example potential points of infiltration sources of water are illustrated in FIG. 1 as points labeled "I." A second source of undesirable external fluids flowing into sewer system 10 is from surface water, i.e., "inflow" flowing into the sewer system. Inflow generally includes water flowing into the sewer system at a relatively high rate for a relatively short period of time. Sources of inflow are typically direct connections to the sewer system, for example, apertures in a manhole cover that permit water from a flooded street to enter the sewer system rather than be directed to the storm sewer system as intended. As previously noted, these undesirable sources of water for sewer system 10 are generally termed "I/I" herein.

Before the sources of I/I in sewer system 10 can be repaired they must first be identified and located. Since the water associated with I/I is generally relatively clean it can be difficult to locate the sources when water is not actively flowing into sewer system 10. The system and method detailed below provides an efficient way to apply a water-responsive indicating coating material to selected portions of a sewer system that are suspected areas of I/I. The indicating coating material is preferably formulated to have suitable surface adherence and water-responsive properties for a particular environment in which it is to be applied. With these characteristics, the effects of infiltration or inflow of water into sewer system 10 will be visually observable for some time after the I/I event by inspecting the condition of the indicating coating material.

The general characteristics of the indicating coating material are preferably such that it sufficiently adheres to the pipes and manhole walls and provides the following desirable water-responsive properties and characteristics. Firstly, the water-responsive properties include a low level resistance and a high level non-resistance. The low level resistance includes substantial maintenance of adhesion of the coating material to a substrate where exposed to high humidity or a relatively low rate of water flow. The indicating coating material is preferably relatively unaffected by high-humidity conditions. Preferably, relatively small amounts of water flowing over the coated surface wears an observable tell-tale path in the indicating coating material. An indicating coating material color that contrasts with the surfaces to which it is applied is also preferable. With such a contrasting color, any discoloration of the indicating coating material is easily visually observable to detect where the highest water level was achieved in the pipe or manhole, which in turn enables maintenance personnel to determine where (i.e., upstream or downstream of the pipe) the I/I problem exists. The high level non-resistance includes erosion of the coating material in the presence of either a relatively high rate of water flow or a lower rate of water flow over a longer period of time. Preferably, to fully remove the indicating coating material from the surface to which it is applied requires a relatively significant flow velocity of water over the surface of the indicating coating material, thus providing again an indication of whether the leakage problem may be upstream or downstream of the coated surface. Where the indicating coating material has been displaced from a specific point on a pipe or manhole, such as at a pipe or manhole joint, preferably indicates that water or I/I flow entered the sewer system at this point in the system. Typically there is a stain beneath that specific point to indicate the intensity of the flow.

A further desired characteristic of the indicating coating material is that it achieve a predetermined tint, such as a yellow tint, in the presence of hydrogen sulfide, thus indicating to maintenance personnel that hydrogen sulfide is present proximate the coated area. Hydrogen sulfide, caused by degrading organic material, is undesirable as it is both toxic and causes biogenic sulfide corrosion in concrete pipe, steel and manholes.

As described above, a desired water-responsive property characteristic of the indicating coating material is that it be water durable and have both low level resistance and high level non-resistance. "Water durable" in the context of the present invention describes an indicating coating material that has low level resistance such that, after application to a substrate in a thin layer, is converted to a solid film that has sufficient adhesion to the substrate to which it is applied that the indicating coating material is not easily wiped away from the substrate. On the other hand, with high level non-resistance, the water durable indicating coating material preferably is not water resistant, so that relatively significant quantities of water flowing across the indicating coating material or impacting the indicating coating material will cause the indicating coating material to erode away in a detectable pattern. Thus, the water durable indicating coating material preferably is effective as an indicator of significant I/I while not being affected by small quantities of water and the high-humidity conditions common in sewer systems, which could lead to false indications of I/I.

It is preferable that the select indicating coating material is formulated such that its change of color or hue in response to its contact with water lasts for a relatively extended period of time, such as a month or more, to enable inspection of the coated surface areas for some duration following one or more I/I events to determine the point source or sources of I/I. Optionally, color pigment of a desired color may be added to the indicating coating material for applying the indicating coating material to white pipes, in order to improve contrast between the coating and the pipe.

In some embodiments of the present invention the indicating coating material may be formulated to adhere to a variety of structural materials such as, but not limited to, pre-cast concrete, ceramic brick and mortar, masonry brick or block/mortar, fiberglass, plastics (PVC or HDPE), limestone/mortar or ceramic clay. The structural material may additionally be lined with concrete, epoxies, fiberglass or sectionalized PVC or HDPE. Indicating coating material may further be formulated for adhesion to these materials. Additives may also be used in connection with indicating coating material such as liquid latex, acrylic binders, for promoting bonding capacity. These additives are particularly useful, for example, when applying a lime indicating coating material to PVC, HDPE and smooth fiberglass surfaces. Preferably, the additives are added to the indicating coating material near to the discharge point of a pump, when a pump is used to apply the indicating coating material.

In some cases the indicating coating material may be a slurry that includes heated water in the range of about 80-120° F. in the initial mixing and makeup of the material. This may reduce the solubility of the solids in the slurry and reduce the tendency of the indicating coating material to run off of coated surface areas.

Figure 2:
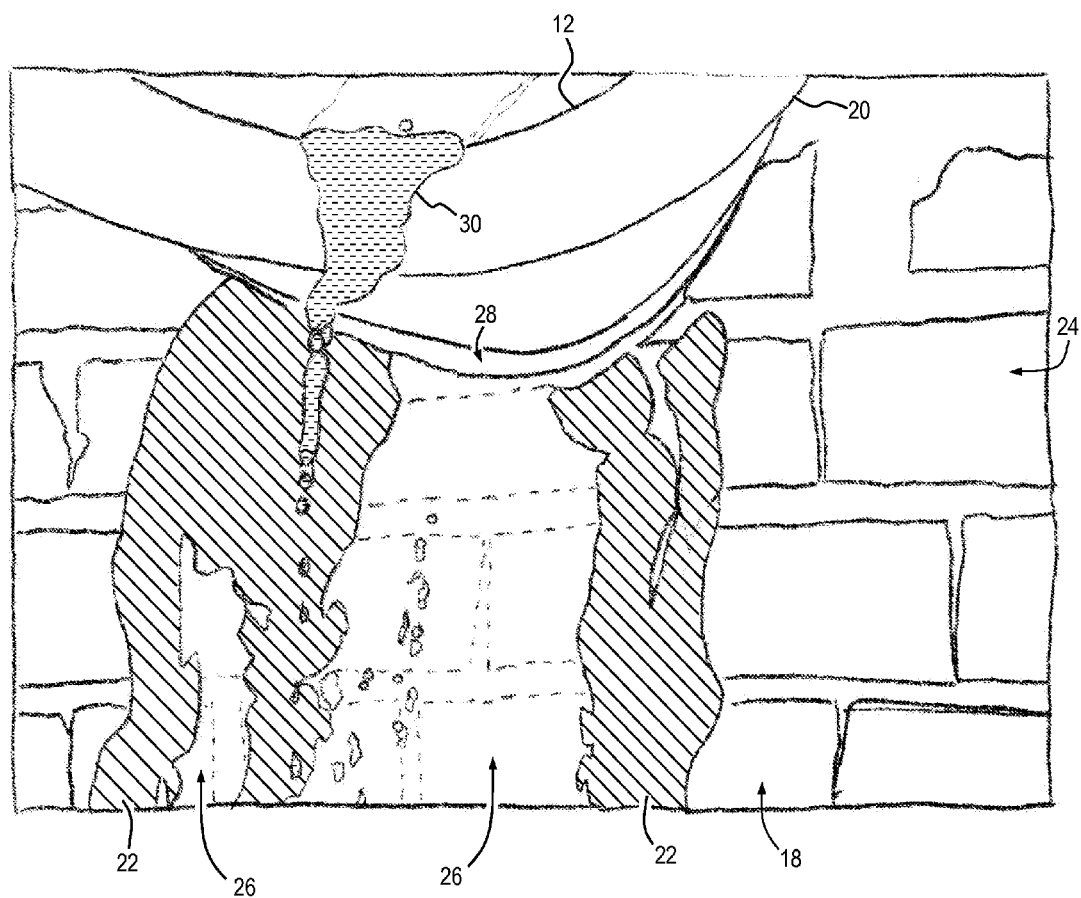
FIG. 2 is an elevational view of the surface of an inner wall of a manhole that is partially coated with an indicative coating and showing an I/I event occurring around the underside of a sewer pipe/manhole junction.

In another embodiment of the present invention the indicating coating material may be configured to indicate the amount of water flow associated with I/I. For example, where the I/I involves a relatively low-velocity flow of water the indicating coating material preferably responds to contact with the water by changing color or hue, but is not removed entirely by the I/I. Conversely, if the I/I involves a higher-velocity flow of water the indicating coating material is substantially entirely removed from the coated surface. This effect can be generally seen in FIG. 2, wherein an indicating coating material 22 which was applied to the surface of an inner wall 24 of a manhole 18, and beneath a sewer main line 12, is washed away from the surface, as depicted by washed area 26, as the result of I/I coming from under the sewer line at a gap 28. Effluent 30 of FIG. 2 is a normally-expected discharge from main line 12.

A preferred indicating coating material for the present invention is a fully-hydrated dolomitic lime composition, hereafter generally termed "lime" indicating coating material. The lime indicating coating material preferably comprises fine particles, allowing the lime indicating coating material to easily flow in applicators such as spray applicators. The lime indicating coating material also preferably easily flows into relatively small areas (e.g., cracks, etc.) when applied to various surfaces of sewer system 10, leaving a relatively homogenous or even coating. The lime indicating coating material typically does not increase the pH of wastewater in sewer system 10 above about 9.5, making it no less than environmentally neutral and particularly compatible with wastewater treatment systems that eventually receive and treat the water flowing in the sewer system. Furthermore, the lime indicating coating material has sufficient adhesive qualities to adhere to the various surfaces of sewer system 10, yet will not bond to the structural material so that it may be purposely flushed out of the sewer system when desired. In one preferred embodiment the lime indicating coating material is a fully hydrated dolomitic lime comprising a concentrated slurry of up to 30% by weight or specific gravity of 1.15%.

The lime indicating coating material preferably has a relatively pure white color for more easily distinguishing any discoloration, staining and erosion (i.e., washing off) due to I/I once it is applied to selected surfaces of sewer system 10.

Although the aforementioned lime indicating coating material is preferred, any suitable water durable indicating coating material configured to indicate the presence of water as described above may be used within the scope of the invention.

A system 48 for applying the indicating coating material to a select portion of sewer system 10 is shown in FIG. 1. A coating tank or reservoir 50 contains a select indicating coating material 22 in a flowable or sprayable form, such as a slurry. Indicating coating material 22 is supplied to an input of a coating pump 54 via a supply line 56 intermediate reservoir 50 and the coating pump. A first end of a generally hollow, flexible hose 58 is coupled to an output or discharge portion of coating pump 54, while a centering cage (also called a "pig") 60 and a nozzle 62 are arranged at a second, opposing end of the hose.

To test main pipe 12 of sewer system 10 hose 58, pig 60 and nozzle 62 are introduced into the main pipe through a suitable access point, such as manhole 18-1, and placed into the main pipe at a predetermined distance. This may be accomplished in several ways. For example, a relatively lightweight string or rope having a weighted end may be tossed from one manhole to another manhole, or may be urged from one manhole to another manhole with a relatively rigid, flexible "fish tape." Alternatively, a lightweight string may be attached to a balloon, the balloon being urged from one manhole to another by flowing air in the pipe, which may be provided by a fan such as fan 78. A heavier string or rope may then be attached to the lightweight string and pulled through the pipe. The heavier string or rope may then be attached to hose 58, pig 60 and nozzle 62 to draw them into the pipe to the desired position. A rigid or semi-rigid object such as a pole may also be used to push hose 58, pig 60 and nozzle 62 to the desired position.

In operation, coating pump 54, when activated, draws indicating coating material 22 from reservoir 50 through supply line 56 and pressurizes hose 58 and nozzle 62 with the indicating coating material, causing the indicating coating material to be dispensed from the nozzle as a spray and deposited upon the selected inner surfaces 64 of pipe 12. Hose 58, pig 60 and nozzle 62 are then withdrawn from main pipe 12 and manhole 18-1 at a predetermined rate while the indicating coating material 22 is being dispensed by the nozzle, thereby coating selected portions of the inner surface of the main pipe with the indicating coating material. Pig 60 aids to keep nozzle 62 generally centered in pipe 12, thus aiding to generally evenly coat the inner surface 64 of the pipe with the indicating coating material. A hose reel 66 may be provided intermediate coating pump 54 and nozzle 62 in order to keep a desired amount of tension on hose 58, and can also be utilized as a manual or motorized take-up device to control the rate at which the hose, pig 60 and nozzle 62 are withdrawn from pipe 12. After the desired portions of main pipe 12 of sewer system 10 are coated coating pump 54 is turned off and hose 58, pig 60 and nozzle 62 are withdrawn from the sewer system through manhole 18-1.

The foregoing discussion of system 48 is directed to main pipe 12 for the purpose of example. Accordingly, one skilled in the art will appreciate that system 48 may likewise be used to coat lateral pipe 20 or any other pipes in sewer system 10.

In another embodiment of the present invention, particularly suitable for coating a select portion of an inner wall 24 of a manhole 18 (e.g., 18-1, 18-2, etc.) spray coating system 48 may be modified by omitting pig 60 and attaching spray nozzle 62 to a controlling device, such as an elongate pole. The indicating coating material 22 may then be applied manually to inner wall 24 by an operator located at the top of the manhole 18 and directing the spray of indicating coating material toward the inner wall. The operator moves nozzle 62 in the manhole with the pole to coat suspected leakage areas with indicating coating material 22. This process does not require the operator to enter the manhole to apply indicating coating material 22.

For the aforementioned coating processes it is preferable to completely coat all surfaces, including gravity main pipe 12, gravity flow sewer lateral lines and manholes 18 with indicating coating material 22. In some embodiments the indicating coating material 22 may be applied at a thickness of about 0.125 inches or less.

The indicating coating material 22 may be maintained in suspension in reservoir 50 of FIG. 1 by a mixer 70 disposed in the reservoir. Optimal pumping of indicating coating material 22 is performed by an air operated diaphragm coating pump 54 where both pressure and volume can be closely controlled. In some embodiments the coating rate for applying indicating coating material 22 is about 1 gallon per 100 square feet of surface area or more or less, depending upon the surface to be coated. A fixed nozzle 62 for application may be configured to provide a generally 360 degree spray pattern in the pipe or manhole to cover the circumference of the pipe or manhole. Alternatively, nozzle 62 may be configured to spray indicating coating material 22 in a predetermined directional pattern.

In some embodiments a filter such as a screen may be utilized to deter large particles of indicating coating material 22 from blocking or plugging the flow of indicating coating material through coating pump 54 and nozzle 62. For example, a well screen 72 may be placed in reservoir 50 and configured to receive at an input portion of the well screen indicating coating material 22. Supply line 56 may be coupled to an output portion of well screen 72 to receive filtered indicating coating material 22. Well screen 72 preferably deters excessive solids of indicating coating material 22 from clogging hose 58 and/or nozzle 62.

With continued reference to FIG. 1, a heated gas 74 such as a gas-fired heater or a vehicle exhaust may optionally be injected into the sewer system being coated. Heated gas 74 may be pressurized for said injection. A fan 76 may also be arranged to draw the heated gas 74 through sewer system 10, for example, manhole 18-1 and the portion of pipe sewer system 10 being coated before being exhausted from manhole 18-2. This provides both a warmer environment within the selected portions of a pipe of sewer system 10 to promote adhesion, and increases the level of $CO_2$ in the pipe which may react with indicating coating material 22 to reduce solubility and enhance adhesion characteristics.

Air flow in selected portions of sewer system 10 during the coating application process may also enhance the spray pattern of indicating coating material 22 and aid in the discharge of the indicating coating material from nozzle 62. Accordingly, fan 76 may be utilized to generate an air flow through the pipes of sewer system 10 selected for coating with indicating coating material 22.

Once coating 22 is applied to the surfaces of sewer system 10 to be treated, subsequent observations of the coated surfaces may be conducted without having to enter a sewer manhole 18 (e.g., 18-1, 18-2, etc.) by using a remote photographic camera and/or video recording system disposed into sewer system 10 to observe indicating coating material 22 for any staining or other degradation. Further details of this process are provided below.

Figure 3:
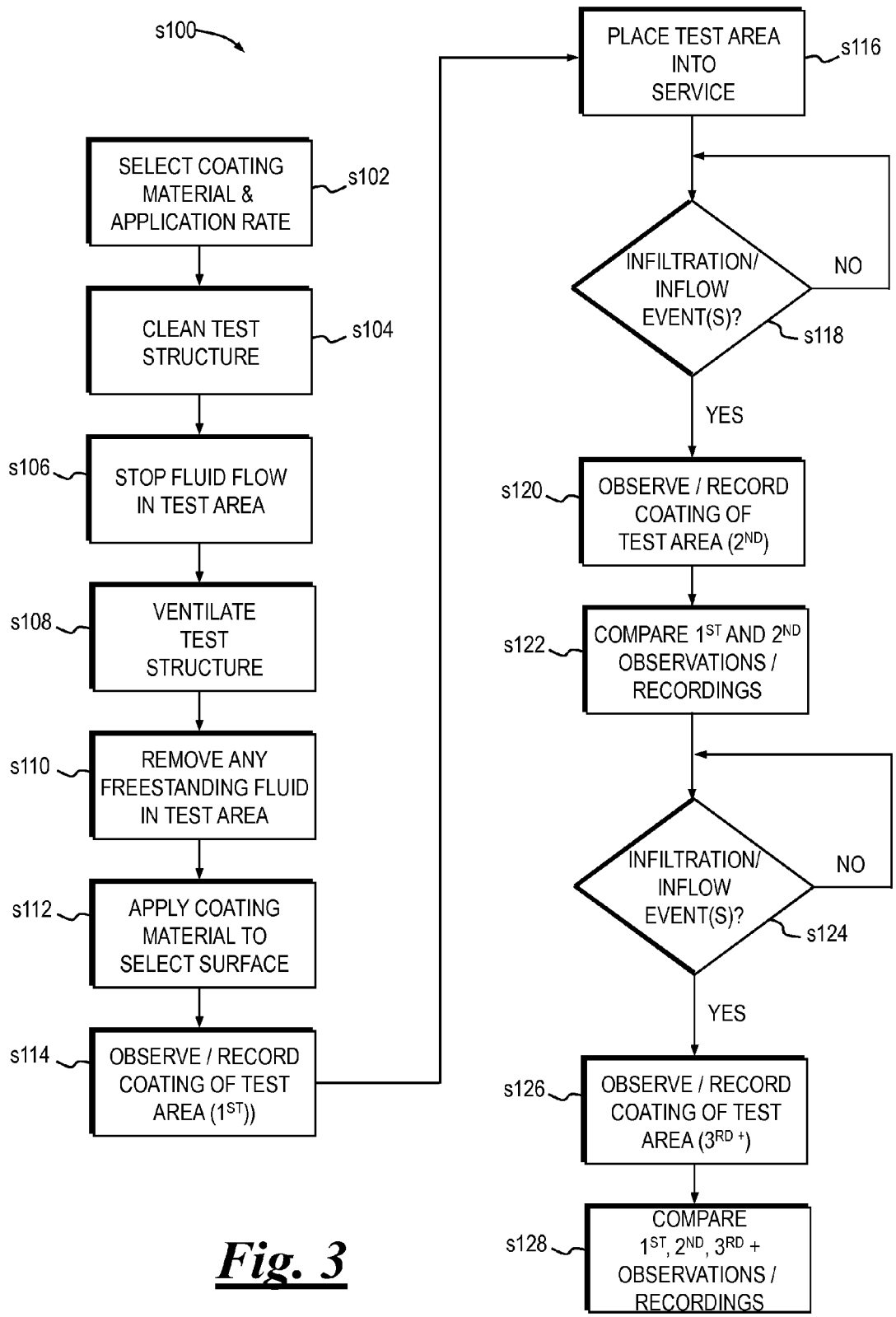
FIG. 3 is a flow diagram depicting a method for detecting sources of I/I in a sewer system according to an embodiment of the present invention.

Referring now to FIG. 3, a process for determining sources of I/I is described at s100. Firstly, a suitable indicating coating material is selected at step s102. As a non-limiting example the aforementioned fully hydrated dolomitic lime slurry may be selected. The selected indicating coating material preferably is water durable as described above and has adhesion, viscosity and water-responsive properties that are optimized for a given surface upon which it is to be applied. Additives such as liquid latex or acrylic binders may optionally be added to the indicating coating material as desired to improve the adhesion quality on such surfaces as PVC or HDPE. The desired application rate for the material to achieve the desired coverage and thickness of the indicating coating material upon the given surface is also determined at s102.

Once the proper indicating coating material and application rate have been selected the surface upon which the coating is to be applied is preferably cleaned of surface debris and coatings, such as slime, mold, sediment and the like at step s104 using conventional means such as pressurized air, scrubbing, swabbing and water knives.

Flow of any materials through the sewer line pipe to be coated may plugged off at step s106 to enable coating of the entire select surface of the pipe. The purpose of this is to prevent significant quantities of water from flowing in the select pipe at the time of application of the indicating coating, which could wash off the indicating coating material. Any suitable plugging device may be used, such as an inflatable plug 78 (FIG. 1).

Once cleaned and free from continued flow of materials, the area to be tested for I/I may be ventilated at step s108, such as with a fan (for example, fan 76 of FIG. 1) in order to dry the surface area to be coated, thus to improving adhesion of the indicating coating material to the test area. In addition, any remaining fluids in the selected test area may be removed at step s110. In gravity sewers, using a multi-stage swab type device pulled through the line to be coated may also be used at s110 to remove free standing water lying in a pipe sag area.

After the surface to be tested has been prepared, the select indicating coating material is applied to the entire inner surface area of the select portion of the sewer system at step s112. It is preferable to fully coat the entire surface and that the indicating coating material substantially infiltrates all cracks, pipe or manhole joints, pipe connections, etc. The indicating coating material 22 may be applied by either a mechanism (e.g., at a controlled rate of travel pulling the nozzle 62 of system 48 through the pipe) or manually by an operator.

Following application of the indicating coating material the initial condition of the indicating coating material is observed and recorded at step s114. This step may be done manually by visually observing the indicating coating material and recording its condition in a report. Alternatively, a photographic or video recorder or any combination thereof may be used to record the condition of the indicating coating material. Reference indicia, such as a tape measure, may be placed within the pipe and associated with the coated surface to establish reference points for use in subsequent inspections. In the alternative, reference indicia such as linear references may be provided by the photographic or video recording equipment and recorded thereon.

After recording the initial condition of indicating coating material 22 the sewer line 12 is placed back into service at s116 by controlled removal of all blockages and opening any previously shut off valves. This lessens a potential rush of water which could prematurely compromise the integrity of the coated walls. Maintenance personnel then wait for a suitable rainfall event at step s118, sufficient to cause I/I. Following such an event the condition of the coated surface is once again visually observed and recorded at s120 in a manner similar to s114. At s122 this subsequent observation is compared to the initial observation to check for observable changes in the pattern (e.g., erosion) of the applied indicating coating material or any change in its color or hue. The comparison may be made visually by maintenance personnel, or may be made using a device such as an image comparator configured to compare observations and indicate any changes such as variations, differences or discrepancies in the observations. If such changes are detected, then the point source of I/I may be readily identified at step s122. If not, the observation process may be repeated, as at steps s124, s126 and s128 until there is evidence of a change in the condition of the indicating coating material. This is due to the fact that I/I leakage points within sewer system 10 may not leak until a rain event of sufficient intensity has occurred.

If, after several observations over various intensity I/I events no change in the indicating coating material is detected, then it may be concluded that no significant I/I is occurring at the area under test. Conversely, signs of I/I may be detected by observing erosion or changes in the color or hue of the indicating coating material. As an example of erosion, in some situations it may be observed that the applied indicating coating material has been eroded away in an area opposite a connecting point of a lateral pipe, indicating significant amounts of fluid flow from the lateral pipe into the main pipe. Similarly, the indicating coating material will show observed maximum depth achieved in the lateral flow or around the lateral pipe connection. Where the coated material is stained to indicate the peak depth achieved in the main pipe or a manhole can also be helpful in defining I/I areas of concern.

For steps s114, s120, s126 signs of I/I impact upon the indicating coating material by using a photographic or video sewer camera.

The above description is for a system and process that allows a sewer system operator to locate and define the location of I/I entering into their sanitary sewer system comprising sewer main lines, manholes/structures and sewer laterals. The system and process also allow for estimating the quantity of I/I that occurred for one or more rain-I/I events. Compared to alternative means of testing, it is a simpler, more cost effective method of locating I/I problems in a sewer system by enabling the determination of the presence or absence of I/I in a sewer lateral, both at the connection point and upstream of the connection point. The presently described disclosure also enables the sewer operator to determine the high flow level that has occurred in the sewer main, manhole/structure and sewer lateral connection point by visually observing the color or hue of the indicating coating material. With the use of video laser profiling equipment and digital imaging methods the extent of a problem can be determined by measuring change in flow pattern, the level of flow, as indicated by the change in color or hue in a pipe or structure and the projected horizontal distance the I/I flowed from the observed defect to another point in the structure.

As previously noted, it is usually not practical for an observer to be present during an I/I event to observe where the I/I is occurring in a sewer system, especially since multiple locations may be under test at any given time. In addition, groundwater or rainwater I/I entering the sanitary sewer system usually does not discolor the surface of the structure long enough to leave a permanent indication of the source of the I/I because it is typically generally clean water. Furthermore, to simulate a water event large enough to trigger I/I into a sewer system for testing requires a significant volume of water to be injected into the ground. The present invention overcomes these drawbacks by providing a reliable, durable indication of the source of I/I since the indicating coating material will be stained and/or washed away by the I/I.

While this invention has been shown and described with respect to several detailed embodiments thereof, it will be understood by those skilled in the art that various changes in form and detail thereof may be made without departing from the scope of the claims of the invention. One skilled in the art will recognize that many of the separately-described elements and steps of the various embodiments of the present invention may be combined, rearranged or eliminated to accomplish the desired result without affecting the scope of the invention. The embodiments disclosed herein are for illustrative purposes only and are not intended to be limiting with regard to the arrangement or combination of the components of the present invention.

What is claimed is:

1. A system for identifying a source of external fluid entering a fluid-carrying structure through at least one of infiltration and inflow, comprising:
   a water durable indicating coating material having water-responsive properties, the water-responsive properties comprising a low level resistance and a high level non-resistance,
   the low level resistance comprising substantial maintenance of adhesion of the coating material to a substrate where exposed to a high humidity or relatively low rate of water flow, and the high level non-resistance comprising erosion of the coating material where exposed to either a relatively high rate of water flow or a lower rate of water flow over a longer period of time;
   an apparatus configured to coat a select portion of the fluid-carrying structure with the water durable indicating coating material;
   an arrangement configured to record the initial condition of the coated surface, and to record subsequent conditions of the coated surface; and
   an arrangement for comparing the initial condition of the coated surface with a subsequent condition of the coated surface to detect if a change in the condition of the coated surface has occurred,
   wherein a predetermined change in the condition of the coated surface identifies the source of external fluid entering the fluid-carrying structure.

2. The system of claim 1 wherein the water durable indicating coating material includes a color pigment.

3. The system of claim 1 wherein the water durable indicating coating material includes an additive to promote bonding of the water durable indicating coating material to the select portion of the fluid-carrying structure.

4. The system of claim 1 wherein the water durable indicating coating material is a slurry that includes heated water in the range of about 80-120° F.

5. The system of claim 1 wherein the water durable indicating coating material comprises a fully-hydrated dolomitic lime composition.

6. The system of claim 5 wherein the fully hydrated dolomitic lime composition comprises a concentrated slurry of up to 30% by weight or specific gravity of 1.15%.

7. The system of claim 1 wherein the coating apparatus comprises:
   a reservoir configured to contain the water durable coating;
   a coating pump communicatively coupled to the reservoir;
   an elongate hose having a first end and a second end, the first end of the hose being coupled to an output of the coating pump; and
   a nozzle coupled to the second end of the hose,
   the coating pump, when activated, drawing the water durable coating from the reservoir and urging the water durable coating through the hose, the water durable coating being sprayed from the nozzle.

8. The system of claim 7, further including a centering cage proximate the nozzle.

9. The system of claim 7, further including a hose reel intermediate the coating pump and the nozzle.

10. The system of claim 7, further comprising a mixer coupled to the reservoir, the mixer being adapted to maintain the water durable indicating coating material in suspension.

11. The system of claim 7, further including a supply line intermediate the reservoir and an input of the coating pump to communicatively couple the reservoir to the coating pump.

12. The system of claim 11, further including a filter having an input portion and an output portion, the filter being configured to receive at the input portion the indicating coating material, the supply line being coupled to the output portion to receive filtered indicating coating material.

13. The system of claim 7, further including a heated gas, the heated gas being configured to be injected into the fluid-carrying structure.

14. The system of claim 13, further including a fan adapted to draw the heated gas through the fluid-carrying structure.

15. The system of claim 1 wherein the recording arrangement comprises at least one of a photographic and a video recorder.

16. The system of claim 15 wherein the recording arrangement further includes reference indicia associated with the coated surface.

17. A method for identifying a source of external fluid entering a fluid-carrying structure through at least one of infiltration and inflow, comprising the steps of:
   selecting a water durable indicating coating material; having water-responsive properties, the water-responsive properties comprising a low level resistance and a high level non-resistance,
   the low level resistance comprising substantial maintenance of adhesion of the coating material to a substrate where exposed to a high humidity or relatively low rate of water flow, and the high level non-resistance comprising erosion of the coating material where exposed to either a relatively high rate of water flow or a lower rate of water flow over a longer period of time;
   applying a coating of the water durable indicating coating material to a select portion of the fluid-carrying structure;
   observing the initial visual condition of the coated surface;
   monitoring for water events that would likely lead at least one of infiltration and inflow of water into the fluid-carrying structure;
   observing a subsequent condition of the coated surface following said water event;
   comparing the initial and subsequent observations of the condition of the coated surface to determine whether there has been a change between the initial and subsequent conditions of the select coated surface; and
   utilizing the comparison to determine whether external fluid is entering the fluid-carrying structure, the comparison further indicating the location of a source of the external fluid in the fluid-carrying structure, when present.

18. The method of claim 17, further including the step of determining an application rate of the water durable indicating coating material.

19. The method of claim 17, further including the step of selecting a fully-hydrated dolomitic lime composition for the water durable indicating coating material.

20. The method of claim 19 wherein the fully hydrated dolomitic lime composition comprises a concentrated slurry of up to 30% by weight or specific gravity of 1.15%.

21. The method of claim 17 wherein the step of applying a coating of the water durable indicating coating material is accomplished with a coating apparatus comprising:
   a reservoir configured to contain the water durable coating;
   a coating pump communicatively coupled to the reservoir;
   an elongate hose having a first end and a second end, the first end of the hose being coupled to an output of the coating pump; and
   a nozzle coupled to the second end of the hose,
   the coating pump, when activated, drawing the water durable coating from the reservoir and urging the water durable coating through the hose, the water durable coating being sprayed from the nozzle.

* * * * *